US006207237B1

(12) United States Patent
Haffner

(10) Patent No.: US 6,207,237 B1
(45) Date of Patent: Mar. 27, 2001

(54) ELASTIC NONWOVEN WEBS AND FILMS

(75) Inventor: William B. Haffner, Kennesaw, GA (US)

(73) Assignee: Kimberly-Clark Corporation, Roswell, GA (US)

( * ) Notice: Subject to any disclaimer, the term of this patent is extended or adjusted under 35 U.S.C. 154(b) by 0 days.

(21) Appl. No.: 09/164,105

(22) Filed: Sep. 30, 1998

(51) Int. Cl.[7] ............... B05D 3/02; B32B 27/04; B32B 27/12; B32B 5/02
(52) U.S. Cl. ............ 427/394; 427/389.9; 427/393.5; 442/62; 442/104; 442/105; 442/164
(58) Field of Search .................. 442/62, 104, 105, 442/164; 427/389.9, 393.5, 394

(56) References Cited

U.S. PATENT DOCUMENTS

| | | |
|---|---|---|
| 3,872,349 | 3/1975 | Spero et al. . |
| 3,911,318 | 10/1975 | Spero et al. . |
| 3,983,039 | 9/1976 | Eastland . |
| 4,042,850 | 8/1977 | Ury et al. . |
| 4,208,587 | 6/1980 | Eastlund et al. . |
| 4,269,581 | 5/1981 | Ury et al. . |
| 4,313,969 | 2/1982 | Matthews et al. . |
| 4,359,668 | 11/1982 | Ury . |
| 4,485,332 | 11/1984 | Ury et al. . |
| 4,507,587 | 3/1985 | Wood et al. . |
| 4,657,802 | 4/1987 | Morman . |
| 4,663,220 | 5/1987 | Wisneski et al. . |
| 4,720,415 | 1/1988 | Vander Wielen et al. . |
| 4,781,966 | 11/1988 | Taylor . |
| 4,789,699 | 12/1988 | Kieffer et al. . |
| 4,965,122 | 10/1990 | Morman . |
| 4,981,747 | 1/1991 | Morman . |
| 5,226,992 | 7/1993 | Morman . |
| 5,324,576 | * 6/1994 | Reed et al. ............... 428/224 |
| 5,336,545 | 8/1994 | Morman . |
| 5,993,922 | * 11/1999 | Babrowicz et al. ............ 428/35.7 |
| 6,005,053 | * 12/1999 | Parikh et al. ............ 525/221 |

FOREIGN PATENT DOCUMENTS

| | | |
|---|---|---|
| 2178433 | 2/1987 | (GB) . |
| 54048865 | 4/1979 | (JP) . |
| 60101124 | 6/1979 | (JP) . |
| 3121139 | 5/1991 | (JP) . |
| 09045146 | 2/1997 | (JP) . |
| 9500333 | 1/1995 | (WO) . |

OTHER PUBLICATIONS

PCT International Search Report dated Mar. 6, 2000.

* cited by examiner

*Primary Examiner*—Terrel Morris
*Assistant Examiner*—Christopher C. Pratt
(74) *Attorney, Agent, or Firm*—Dority & Manning, P.A.

(57) ABSTRACT

The present invention is generally directed to elastic nonwoven webs and films made from thermoplastic polymers. In particular, the present invention is directed to forming nonwoven webs and films from an elastomeric polymer and then cross-linking the polymer in order to improve the stretch characteristics of the article. Cross-linking also makes the article more temperature resistant. in one embodiment, the elastomeric polymer is a metallocene-catalyzed copolymer of polyethylene. Elastic layers made in accordance with the present invention can be combined into laminates and used in various products, such as diapers and other personal care articles.

12 Claims, No Drawings

ELASTIC NONWOVEN WEBS AND FILMS

FIELD OF THE INVENTION

The present invention is generally directed to a process for cross-linking thermoplastic polymers used to make fibers and films in order to improve their temperature resistance and to decrease the amount of stress-relaxation that the fibers and films may undergo during use. More particularly, the present invention is directed to cross-linking metallocene-catalyzed elastomeric polymers contained in fibers and films which are used in elastic stretch-bonded and neck-bonded laminates.

BACKGROUND OF THE INVENTION

Webs, films, and laminates made from low density, high comonomer content elastomeric fibers and films are used for a variety of applications where stretchability is required. For instance, waist bands, leg bands, feminine care products, adult care products, and diapers employ elastic components in order to supply such articles with elastic properties and a better fit.

Various methods for producing such elastic products have been previously disclosed in the past. For instance, in U.S. Pat. No. 4,663,220 to Wisneski et al., which is incorporated herein by reference in its entirety, the synthesis of elastomeric products from polyolefin-containing extrudable materials is disclosed. In this reference, extrudable elastomeric compositions are formed by blending an A-B-A' block copolymer (where "A" and "A'" are each a thermoplastic endblock including styrene and where "B" is an elastomeric midblock) with a polyolefin. The above polymer blend is extrudable when subjected to elevated pressure and temperature conditions. The A-B-A' block copolymer imparts elastic properties to products formed from the composition.

Such compositions are extruded by being molded at an appropriate combination of elevated pressure and temperature. The pressure and temperature will vary depending on the polyolefin utilized. These extrudable compositions may be formed into a variety of products such as fibrous nonwoven elastomeric webs with varying basis weights. Herein, the terms "elastic" and "elastomeric" are used to refer to materials that, upon application of a force, are stretchable to a stretched length of about 125 percent of their original relaxed length.

However, when such elastomeric materials are released from a stretched position, the fibers typically do not return to their original relaxed length, but exhibit permanent elongation. For example, if an elastic laminate is stretched over a surface and left in this stretched or stressed situation for a period of time, the resistive forces that the elastomeric fibers in the laminate exert on the surface diminish. Thus, when the laminate is removed from the surface and released from its stretched position, the fibers within the laminate will have become permanently elongated when relaxed, reducing the stretch characteristics of the fabric. This elongation process is known as stress relaxation.

When such stress relaxation occurs within elastomeric fibers, the performance of such fibers is negatively affected. Fibers that have undergone significant stress relaxation will not supply laminates with needed fit properties and holding power.

Thus, a need currently exists for a process to improve the performance of elastomeric fibers so that they will undergo significantly less stress relaxation.

SUMMARY OF THE INVENTION

The present invention recognizes and ameliorates the foregoing problems and others experienced in the prior art.

The present invention is generally directed to a process for cross-linking elastomeric polymers, such as metallocene-catalyzed polymers, contained within elastic fibrous webs, laminates, films, foams and the like. For example, metallocene-catalyzed elastic fibers and films can usually contain elastomers which are metallocene-catalyzed from ethylene and a comonomer such as butene, hexene, octene, and the like. The polymers are low-density because of their short chain branching (as opposed to typical high density polymers which do not normally contain a significant amount of chain branching). The polymeric chains contained within the elastomeric polymers are normally not chemically bonded together. A cross-linking process, however, creates bonding between the chains, making fibers and films made from the polymer stronger, more temperature resistant, and less likely to undergo significant stress relaxation.

According to the present invention, there are several methods available in order to cross-link the elastomers contained within the fibers and films. For instance, the elastomers can be cross-linked by exposing the fiber or film to electron beam irradiation.

In an alternative embodiment, a cross-linking agent can be combined with the elastomers which initiates cross-linking after the fibers and films have been formed. For example, in one embodiment, the cross-linking agent can be a peroxide which causes the elastomers to cross-link when exposed to heat.

In another alternative embodiment, a silane can be used as a cross-linking agent. Silane will cause the elastomers to cross-link when exposed to moisture and a catalyst, such as a tin catalyst.

In a further alternative embodiment, the cross-linking agent can be a photoinitiator, which initiates cross-linking of the elastomers when subjected to electromagnetic radiation, such as ultraviolet radiation.

Other objects, features and aspects of the present invention are discussed in greater detail below.

DETAILED DESCRIPTION OF PREFERRED EMBODIMENTS

It is to be understood by one of ordinary skill in the art that the present discussion is a description of exemplary embodiments only, and is not intended as limiting the broader aspects of the present invention, which broader aspects are embodied in the exemplary construction.

The present invention is generally directed to a process for cross-linking elastomeric polymers and particularly metallocene-catalyzed elastomers. Fibers, films, and foams made from such elastomers typically comprise linear low density polyethylene with a high comonomer content. Because of their stretch properties, these types of articles are commonly used in elastic laminates and other elastic-type products. The comonomer may be butene, hexene, octene, or the like. In a preferred embodiment of this invention, the comonomer is octene.

Cross-linking elastic polymers, which are used to form fibrous webs, films and foams in accordance with the present invention, offer many advantages, especially in applications where the stretch properties of the polymer are utilized. For instance, cross-linking the polymer has been found to improve the temperature resistance of the polymer, making the polymer better suited for higher temperature applications. Cross-linking elastomeric polymers in accordance with the present invention also reduces stress-relaxation of the polymer. Consequently, when used in elastic applications, elastomeric polymers cross-linked in accordance with the present invention maintain their elastic properties for a longer period of time and are less prone to becoming irreversibly damaged due to over-stretching.

In the present invention, an elastic laminate is a product comprising two or more layers, such as foams, films and/or nonwoven webs, bonded together to form a laminate wherein at least one of the layers has the characteristics of an elastic polymer. Examples of elastic laminates include, but are not limited to, stretch-bonded laminates and neck-bonded laminates.

"Stretch-bonded" refers to an elastic member being bonded to another member while the elastic member is extended at least about 25 percent of its relaxed length. "Stretch-bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered. Such a multilayer composite elastic material may be stretched until the nonelastic layer is fully extended. One type of stretch-bonded laminate is disclosed, for example, in U.S. Pat. No. 4,720,415 to Vander Wielen et al., which is incorporated herein by reference. Other composite elastic materials are described and disclosed in U.S. Pat. Nos. 4,789,699 to Klaffer et al., U.S. Pat. No. 4,781,966 to Taylor, U.S. Pat. No. 4,657,802 to Morman, and U.S. Pat. No. 4,655,760 to Morman et al., all of which are incorporated herein by reference thereto.

"Neck-bonded" refers to an elastic member being bonded to a non-elastic member while the non-elastic member is extended or necked. "Neck-bonded laminate" refers to a composite material having at least two layers in which one layer is a necked, non-elastic layer and the other layer is an elastic layer. Examples of neck-bonded laminates are such as those described in U.S. Pat. Nos. 5,226,992, 4,981,747, 4,965,122, and 5,336,545, all to Morman and all of which are incorporated herein by reference thereto.

The elastic member used in stretch-bonded laminates, neck-bonded laminates and in other similar laminates can be a film, for example a microporous film, a fibrous web, such as a web made from meltblown fibers, or a foam. The film can be formed by extruding a filled elastomeric polymer and subsequently stretching it to render it microporous.

Fibrous elastic webs can also be formed from an extruded polymer. For instance, as stated above, in one embodiment the fibrous web can contain meltblown fibers. The fibers can be continuous or discontinuous. Meltblown fabrics have been conventionally made by extruding a thermoplastic polymeric material through a die to form fibers. As the molten polymer fibers exit the die, a high pressure fluid, such as heated air or steam, attenuates the molten polymer filaments to form fine fibers. Surrounding cool air is induced into the hot air stream to cool and solidify the fibers. The fibers are then randomly deposited onto a foraminous surface to form a web. The web has integrity but may be additionally bonded if desired.

Besides meltblown webs, however, it should be understood that other fibrous webs can be made in accordance with the present invention. For instance, in an alternative embodiment, it is believed that elastic spunbond webs can also be formed. Spunbond webs are typically produced by heating a thermoplastic polymeric resin to at least its softening temperature, then extruding it through a spinnerette to form continuous fibers, which can be subsequently fed through a fiber draw unit. From the fiber draw unit the fibers are spread onto a foraminous surface where they are formed into a web and then bonded such as by chemical, thermal or ultrasonic means.

As described above, the present invention is particularly directed to cross-linking elastomeric polymers in order to improve their stretch properties. In general, preferably the elastomeric polymer is cross-linked after the elastic film or fibrous web is formed. In some applications, when the elastic layer is combined into a laminate product, the elastomeric polymer can be cross-linked after the laminate has been formed.

The manner in which the elastomeric polymer is cross-linked in accordance with the present invention can vary depending upon the circumstances and the desired results. For instance, in one preferred embodiment of the present invention, elastic fibrous webs or films can be exposed to electron beam irradiation which causes the elastomeric polymer contained within the fibers and films to cross-link. Electron beam irradiation bombards the polymer chains, such as polyethylene chains, with high energy radiation, which can rip hydrogen atoms from the chains creating reactive radical sites which cause the polymer to cross-link.

Using electron beam irradiation to cross-link the elastomeric polymer offers various advantages with respect to the present invention. In particular, electron beams are capable of penetrating through the entire thickness of many films and fibrous webs. Further, it is believed that an electron beam can even be used to cross-link an elastomeric polymer contained within a laminate product. Thus, according to the present invention, elastic laminate products can be formed and then subsequently subjected to an electron beam in order to cross-link the elastomeric polymer contained within the laminate. Further, electron beam irradiation causes cross-linking very rapidly and can be used in a continuous process according to the present invention.

In an alternative embodiment, however, a cross-linking agent can be added to the elastomeric polymer prior to formation of a fibrous web or film. For instance, in one embodiment, a peroxide is added to an elastomeric polymer, such as polyethylene. Peroxide addition can cause cross-linking of polyethylene during melting, extrusion, and spinning processes. For example, heat in an extruder can be used to create free radical sources via the peroxide. The free radicals transfer to the polyethylene, initiating the cross-linking reaction. The degree of cross-linking is controlled by the amount of peroxide that is added to the polymer.

In an alternative embodiment, silane can be added to polyethylene in combination with a peroxide in order to cause cross-linking. The addition of silane creates a grafting process where free radicals form reactive sites on the polymer chain, such as a polyethylene chain. The silane molecules, however, quench the radical sites and therefore do not cause cross-linking to occur immediately. In order for cross-linking to occur, the polymer can be contacted with water and a catalyst, such as a tin catalyst which in one embodiment may be di-butyl tin dilaurate. The water and catalyst are needed to create a grafted structure. Of particular advantage, cross-linking using a silane can be delayed and controlled until the addition of water.

In a further alternative embodiment of the present invention cross-linking in the polymer, particularly polyethylene, is accomplished by adding a photoinitiator to the polymer. Once a photoinitiator is added to the polymer, cross-linking of the polymer occurs when the polymer is exposed to electromagnetic radiation, and in particular, ultraviolet radiation. Ultraviolet light breaks bonds in the additive creating free radicals which then propagate a cross-linking reaction. Similarly to the reaction involving silane, in this embodiment, cross-linking can occur at any point in the process of forming the fiber, in forming a nonwoven web incorporating the fiber, or in forming a film.

Various photoinitiators can be used according to the process of the present invention. Preferably, a photoinitiator is chosen that can withstand extrusion temperatures without degrading or reacting. Examples of photoinitiators that may be used in the process include IRGACURE 369, or IRGACURE 907, which are available from the Ciba Speciality Chemicals Corporation of Terrytown, N.Y.

The elastomeric polymers that can be cross-linked and used in elastic applications according to the present invention may vary. In general, preferably the elastomeric polymer is a copolymer of a polyolefin, such as a copolymer of polyethylene or possibly polypropylene. The polyolefin can be copolymerized with various monomers including, for instance, octene, butene, hexene and mixtures thereof.

In one preferred embodiment of the present invention, a metallocene-catalyzed elastomeric copolymer is used.

As used herein, a metallocene catalyst refers to a metal derivative of cyclopentadiene and can be described as a homogeneous single site or constrained geometry catalyst. A metallocene is a neutral, ancillary ligand stabilized transition metal complex and can have the following general formula:

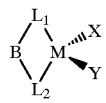

wherein:
  $L_1$ is a cyclopentadienyl or substituted cyclopentadienyl moiety bonded to the metal through η-5 bonding
  $L_2$ is an organic moiety, which may or may not be a cyclopentadienyl moiety, strongly bonded to the metal which remains bonded to the metal during polymerization
  B is an optional bridging group that restricts the movement of $L_1$ and $L_2$ and that modifies the angle between $L_1$ and $L_2$
  M is a metal such as, for instance, titanium or zirconium
  X and Y are halides or other organic moieties, such as methyl groups For instance, in one embodiment, metallocene can be as follows:

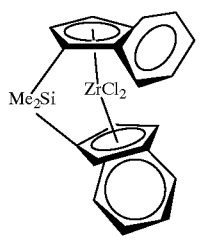

The metallocene-catalyzed elastomeric polymer can be a copolymer of ethylene and another monomer, such as octene, butene, hexene or mixtures thereof. The monomer can be present in the copolymer in an amount up to about 30% by weight, particularly from about 7% to about 25% by weight, and preferably from about 14% to about 25% by weight. Preferably, the other monomer copolymerized with ethylene is octene. The elastomeric polymer can have a low density ranging from about 0.85 g/cc to about 0.92 g/cc, and particularly from about 0.86 g/cc to about 0.90 g/cc.

Commercially available metallocene-catalyzed elastomeric polymers that can be used in the present invention include the Dow Plastics AFFINITY polymers having product numbers EG 8100, EG 8200, or EG 8150 which all contain from about 23% to about 25% octene. In an alternative embodiment, Dow Plastics AFFINITY polymer PT 1450 is used, which contains approximately 13.8% by weight octene and has a density of about 0.902 g/cc. It has been discovered that these polymers not only have good elastic properties, but are also capable of being cross-linked according to the present invention.

Specifically, it is believed that cross-linking the above described elastomers provides the elastomers with a set molecular structure. The set molecular structure causes nonwoven webs and films made from the polymers to have increased temperature resistance and improved stress relaxation properties.

Elastic fibrous webs and films made according to the present invention can be incorporated into a diverse variety of products where stretch properties are desired. The elastic nonwoven webs and films, for instance, can be used alone or can be incorporated into a laminate, such as a stretch-bonded laminate or a neck-bonded laminate as described above. When incorporated into a laminate, the elastic layer made in accordance with the present invention is typically attached to at least one other non-elastic layer, such as a nonwoven spunbond web. In one embodiment, an elastic layer made in accordance with the present invention can be placed in between a first outer spunbond layer and a second outer spunbond layer. The elastic layer can be thermally bonded to the spunbond layers or attached according to any other suitable method. The nonelastic layers are generally combined with the elastic layer in a manner that allows the elastic layer to stretch and contract.

Once produced, the laminates of the present invention can be used in many different and various products. For instance, the laminates can be used in liquid absorbent products, in personal care articles, in garments, and in various other products. For example, in one embodiment, an elastic laminate made in accordance with the present invention can be used as an elastic member incorporated into a diaper or other similar product. The elastic laminate can be used to comfortably secure the diaper or other similar garment to the user.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:
1. A process for producing an elastic laminate comprising the steps of:
   extruding an elastomeric polymer into an elastic layer;
   cross-linking said elastomeric polymer an amount sufficient to improve the stress-relaxation properties of said elastic layer; and
   attaching said elastic layer to an extendable non-elastic layer in a manner that allows said elastic layer to be stretched and contracted, said non-elastic layer comprising a fibrous web.

2. A process as defined in claim 1, wherein said elastomeric polymer comprises a copolymer of a polyolefin.

3. A process as defined in claim 2, wherein said copolymer comprises a metallocene-catalyzed copolymer of ethylene and a comonomer selected from the group consisting of butene, octene, hexene and mixtures thereof, said comonomer being present within said copolymer in an amount up to about 30% by weight.

4. A process as defined in claim 3, wherein said comonomer comprises octene, said octene being present within said copolymer in an amount from about 7% to about 25% by weight.

5. A process as defined in claim 1, wherein said elastic layer comprises a fibrous web.

6. A process as defined in claim 5, wherein said fibrous web comprises a meltblown web.

7. A process as defined in claim 1, wherein said elastic layer comprises a film.

8. A process as defined in claim 1, wherein said elastomeric polymer is cross-linked by exposing said elastic layer to electron beam irradiation.

9. A process as defined in claim 1, wherein said elastomeric polymer contains a photoinitiator, and wherein said elastomeric polymer is cross-linked by exposing said elastic layer to ultraviolet radiation, said ultraviolet radiation activating said photoinitiator for causing said polymer to cross-link.

10. A process as defined in claim 1, wherein said elastomeric polymer contains a cross-linking agent for initiating cross-linking of said polymer.

11. A process as defined in claim 10, wherein said cross-linking agent comprises a peroxide.

12. A process as defined in claim 10, wherein said cross-linking agent comprises a silane.

* * * * *